United States Patent
He et al.

[11] Patent Number: 6,074,998
[45] Date of Patent: Jun. 13, 2000

[54] BAR COMPOSITIONS COMPRISING AMPHIPHILIC POLYOL ESTER STRUCTURANT WHICH RELEASES OIL

[75] Inventors: Mengtao He, Wayne; Michael Barratt, Palisades Park; James Dalton, Cliffside Park; Michael Fair, Hackensack, all of N.J.; Michael Petko, Mt Vernon; John Sheehan, Brooklyn, both of N.Y.; Abid Khan-Lodhi, North Bergen, N.J.

[73] Assignee: Lever Brothers Company, New York, N.Y.

[21] Appl. No.: 09/012,990

[22] Filed: Jan. 26, 1998

[51] Int. Cl.[7] ....................................................... A61K 7/50
[52] U.S. Cl. .......................... 510/155; 510/141; 510/151; 510/156
[58] Field of Search .................................... 510/141, 152, 510/151, 155, 156, 447

[56] References Cited

U.S. PATENT DOCUMENTS

| | | |
|---|---|---|
| 4,551,332 | 11/1985 | Stillman . |
| 4,664,914 | 5/1987 | Stillman . |
| 4,976,953 | 12/1990 | Orr et al. ................................... 424/47 |
| 5,154,849 | 10/1992 | Visscher et al. . |
| 5,510,050 | 4/1996 | Dunbar et al. . |
| 5,554,315 | 9/1996 | Tonomura et al. . |
| 5,817,609 | 10/1998 | He et al. . |

FOREIGN PATENT DOCUMENTS

| | | |
|---|---|---|
| 0617955 | 10/1994 | European Pat. Off. . |
| 1570142 | 6/1980 | United Kingdom . |
| 92/13060 | 8/1992 | WIPO . |

Primary Examiner—Necholus Ogden
Attorney, Agent, or Firm—Ronald A. Koatz

[57] ABSTRACT

The present invention relates to solid detergent compositions generally comprising anionic/amphoteric/nonionic surfactant systems. Addition of specific polyol esters wherein the melting temperature and HLB are specifically defined has been found to remarkably enhance the oil/humectant structuring and releasing capabilities of a skin cleansing bar. In a second embodiment, the invention relates to a method for enhancing the bar's capability of including high levels of oil and/or humectant by carefully balancing the polyol ester's weight ratio to the oil and/or humectant. In the third embodiment, the invention relates to a method of enhancing the bar's capability of incorporating high levels of oil and/or humectant and delivering the oil and/or humectant for skin benefit by carefully balancing the polyol ester's weight ratio to the other costructurants such as PEG 8000 and fatty acid. In the third embodiment, skin mildness and especially skin moisturization are significantly enhanced by the detergent bar compositions comprising the combination of the specific polyol ester with oil and/or humectant.

21 Claims, 1 Drawing Sheet

BAR COMPOSITIONS COMPRISING AMPHIPHILIC POLYOL ESTER STRUCTURANT WHICH RELEASES OIL

FIELD OF THE INVENTION

The present invention relates to personal wash bar compositions, particularly compositions comprising (1) one or more surfactants, (2) one or more liquid emollient oils and/or humectants, and (3) a solid polyol ester with specifically defined HLB and melting temperature. The invention relates to structuring high levels of emollient oils and/or humectants in solid bar matrixes using the specific polyol ester solid. Through careful balancing of the polyol ester to oil and/or humectant ratio, and carefully balancing the structuring systems for the oil domain and surfactant domain in the solid bar, a novel approach of delivering mild, moisturizing ingredients to the skin via personal wash is developed.

BACKGROUND

It is technically difficult to include high levels (e.g., 10–20%) of liquid hydrophobic emollient oil (e.g., sunflower seed oil) and/or hydrophilic liquid humectant (e.g., glycerin) in a solid personal washing bar form and meanwhile maintain the bar mildness and benefit delivery to the human skin.

For example, high levels of humectants (e.g., glycerin, low MW polyalkylene glycol) can be trapped in a solid matrix of caboxylic fatty acid soap bar. However, it is known that carboxylic soap is harsh to skin especially when the soap concentration is high and when the soap is dissolved in the aqueous washing liquor through its own hydrophilic tendency or through the act of cosurfactants in the bar.

On the other hand, non-soap synthetic bar formulations are primarily structured by either hydrophobic crystalline materials such as free fatty acid or paraffin wax or by hydrophilic crystalline materials such as polyalkylene glycol of high molecular weight (e.g., MW between 2000 and 20000). While not wishing to be bound by theory, formulating high levels of emollient oil into a bar structured by the hydrophobic crystalline materials is believed to result in tightly binding the oil with the hydrophobic crystalline structurants. This contributes to the incapability of releasing the oil to water from the bar and may prevent delivering the oil to the skin via personal wash (see Example 1). Including liquid oils and/or liquid humectants in bars structured by hydrophilic crystalline materials leads to another difficulty. That is, the oil and the humectant are not compatible with the hydrophilic structurants, and this incompatibility results in oil leakage and phase separation from the bulk portion of the bar (see Example 1).

Therefore, a novel mild bar structuring system is required to be able to satisfactorily structure the oil and/or the humectant in the bar while simultaneously permitting oil release from the bar to the aqueous liquid and then to the human skin via the route of personal wash.

Novel to the art, the applicants of the subject invention found a specific group of polyol esters (i.e., having specific ranges of HLB and specific melting temperature) are capable of both structuring a high level of hydrophobic emollient oils and/or humectants in solid personal washing bars while still permitting the oil and humectants to be released from the bar into aqueous liquor to be delivered to the human skin through the route of personal wash. Using the polyol esters with specific hydrophilic-lipophilic balance (HLB), balancing the ratio between polyol ester and oil/humectant, and balancing the ratio between polyol ester to other structurants are critical to achieve the desired oil structuring and oil releasing.

The use of polyol esters in personal washing bars is not new.

European Patent Application EP 94105052.8 assigned to Kao Corp. (invented by M. Tonomura and T. Ohtomo), for example, teaches the use of monoglycerides to boost the lather of formulations comprising only nonionic surfactants. The application does not teach the use of the combination of specific solid monoglycerides and high level of liquid emollient oils/humectants to make bars, preferably pourable, cast melt bars, preferably comprising anionic surfactants and amphoteric surfactants. By contrast, the subject invention found that by using a specific polyol ester (e.g., specific range of HLB, polyol ester to oil/humectant ratio, and polyol ester to other structurant ratio), high levels of emollient oil and/or humectants can be satisfactorily incorporated into bars for skin benefit.

An international application published under PCT WO 92/13060 to Procter & Gamble (authored by R. James) teaches the use of monoglycerides in general, PEG and fatty acid as binders for an extruded syndet bar formulation. The prior art, however, does not teach the use of a specific combination of specific monoglycerides (e.g., specific ranges of HLB) and PEG and fatty acid to incorporate high level of liquid emollients (e.g., vegetable oils)/liquid humectants (e.g., glycerin) to make a bar, preferably pourable, cast melt bar. The prior art also does not teach the specific bar formulation spaces to ensure that high levels of liquid oils and/or humectants can be structured in the solid bar matrixes and can be delivered to skin via personal wash. In contrast, the subject invention found that by using a specific polyol ester (e.g., polyol esters with specific range of HLB, specific polyol ester to oil ratio, and specific polyol ester to other structurant (e.g., PEG and fatty acid) ratio), high levels of emollient oil and/or humectants can be satisfactorily incorporated into bars and can be delivered from the bars to skin under the personal wash condition.

U.S. Pat. No. 5,510,050 to J. Dunbar, P. Beerse, and E. Walker also teaches the use of monoglycerides in general as a non-preferred candidate for the plasticizers in an extruded cleansing bar containing liquid polyols (4–15%) and magnesium soap (4.5 to 50%). The preferred plasticizers are fatty acids, sodium soap, and paraffin wax (Column 5, line 22–24). The prior art, however, does not teach the use of a specific combination of specific monoglycerides (e.g., specific ranges of HLB) and other plasticizers to incorporate high level of liquid emollients (e.g., vegetable oils)/liquid humectants (e.g., glycerin) into a bar, preferably pourable, cast melt bar. The prior art also does not teach the specific bar formulation spaces to ensure that high levels of liquid oils and/or humectants can be structured in the solid bar matrixes and can be delivered to skin via personal wash. In fact, as found by the subject invention, the preferred plasticizers used in the prior art hinder the skin deposition of liquid oils from bars to skin. The prior art has to use magnesium soap as the key ingredient to aid processing (column 2, line 26). In contrast, the subject invention found that by using a specific polyol ester (e.g., polyol esters with specific range of HLB, specific polyol ester to oil ratio, and specific polyol ester to other structurant (e.g., PEG and fatty acid) ratio), high levels of emollient oil and/or liquid humectants can be satisfactorily incorporated into bars and can be delivered from the bars to skin under the personal wash condition. In the subject invention, carboxylic acid soap in general is an optional ingredient. Said soap causes skin irritation and is preferred to be used at about below 4% wt. of total bar composition in the subject application.

A Great Britain Patent GB 1,570,142 assigned to GAF Corp. teaches the use of both hardened triglycerides and fatty alcohols as the plasticizers in an extruded syndet formulation. In contrast to the subject invention, the prior art does not teach the use of the combination of specific monoglycerides and high level of liquid emollient/humectants to make bars. By contrast, the subject invention found that by using a specific polyol ester (e.g., specific range of HLB, polyol ester to oil ratio, and polyol ester to other structurant ratio), high levels of emollient oil and liquid humectants can be satisfactorily incorporated in the bar and can be delivered to skin via skin cleansing for the purpose of skin moisturization.

In summary, none of the references, alone or in combination teach that the use of specific polyol esters (e.g., having specific melting temperature, especially specific hydrophobic-lipophobic balance (HLB)) in specific bar compositions (i.e., containing greater than or equal to 5% hydrophobic emollient oils and/or humectants, the polyol ester to oil/humectant ratio greater or equal to 1:1, and the polyol ester to other structurant ratio greater than 1:1) will result in bars, preferably pourable cast melt bars, with enhanced oil/humectant carrying and releasing capabilities. These capabilities are crucial to benefit delivery to the skin via personal wash.

BRIEF SUMMARY OF THE INVENTION

Unexpectedly, applicants have found that in personal wash bar compositions comprising (%: percentage in weight):

(a) 5% to 70%, preferably 10% to 60%, total composition of surfactant or mixtures of surfactants; and (b) 5% to 40%, preferably 10% to 25% total bar composition of a liquid hydrophobic emollient oil, liquid hydrophilic humectant or a mixture thereof;

(c) 15% to 70%, preferably 20% to 50%, total composition of a solid amphiphilic polyol ester with general molecular structure described as in which POL represents the polyol moiety, R represents an organic hydrophobic group (e.g., straight or branched chain C8–C24 alkyl or alkylene), and one or more R—(C=O)—O— functional groups are chemically attached to one or more of the hydroxy groups of the polyol moiety (POL); said solid, amphiphilic polyol ester having a hydrophilic-lipophilic balance (HLB) number at between 2 and 1 5, preferably between 2.5 and 10, more preferably between 3 and 8;

said polyol ester having melting temperature at between 40° C. and 90° C., preferably at between 45° C. and 70° C.;

the weight ratio of said polyol ester to the sum of said emollient oil and/or humectants (b) being greater than or equal to 1: 1, preferably greater than or equal to 1.5:1, most preferably greater than or equal to 2.0:1;

said solid, amphiphilic polyol ester include but not being limited to glycerin fatty esters, such as glyceryl monolaurate and glyceryl monostearate; alkylene glycol fatty esters, such as ethylene glycol monostearate and ethylene glycol monolaurate; pentaerythrityl fatty esters such as pentaerythrityl stearate; polyglycerin fatty esters such as hexaglyceryl tristea rate;

(d) 0 to 30%, preferably 5 to 20% an optional structurant, the total weight percentage of the said optional structurant (d) has to be less than the total weight percentage of the said polyol ester described in (c). This specification is a criticality because otherwise the bar will have its oil structuring capability reduced, which causes oil leakage and/or oil phase separation from the bulk (see Example 1 and 2); or the bar will have its oil releasing capability reduced, which prevents the oil from releasing into the aqueous washing liquor and delivering to the skin via the personal washing route (see Example 1);

such that high levels of lipophilic oils and/or liquid humectants can be satisfactorily incorporated in the solid matrixes of the bars while retaining the releasing ability to deliver preferred skin benefits to skin via skin cleansing.

DETAILED DESCRIPTION OF THE INVENTION

The present invention relates to novel personal washing bar compositions, particularly compositions in which the surfactant system comprises greater than 5%, preferably greater than 10% emollient oil and humectant. The bar is primarily structured by a specific polyol ester with defined range of HLB and melting temperature.

Unexpectedly, applicants have found that when the HLB of the solid polyol ester is between 2 and 15, preferably between 2.5 and 10, most preferably between 3 and 8, high levels of the emollient oil and/or humectant can be satisfactorily structured in the solid bar matrix, and the bar permits oil and/or humectant to be released to aqueous washing liquid to be delivered to the skin via personal wash.

In order to ensure that the oils are satisfactorily structured in the solid bar matrixes and can be released from the bar into aqueous personal wash liquor, the weight ratio of the polyol esters to the oil and/or humectants has to be greater than or equal to 1:1, preferably greater than or equal to 1.5:1, and most preferably greater than or equal to 2:1. For the same purpose, the weight ratio of the polyol esters to other optional structurants has to be above 1:1.

The compositions are defined in greater detail below:

(a) Surfactant System

The surfactant system of the subject invention generally comprises 5% to 70%, preferably 10% to 60%, most preferably 15% to 40% total composition surfactant or mixtures of surfactants. The surfactants generally comprise anionic surfactants, amphoteric surfactants, nonionic surfactants, cationic surfactants and mixtures thereof, preferably anionic surfactants, amphoteric surfactants, nonionic surfactants and mixtures thereof.

Anionic Surfactants

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation;
amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R\!-\!O\!-\!(CH_2CH_2O)_n\overset{O}{\overset{\|}{C}}CH_2CH(SO_3M)CO_2M$$

wherein n = 1 to 20; and M is as defined above.
Sarcosinates are generally indicated by the formula $$RCON(CH_3)CH_2CO_2M,$$

wherein R ranges from $C_8$–$C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R\!-\!(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ$^{(R)}$ by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Iardi et al., U.S. Pat. No. 5,393,466, hereby incorporated by reference into the subject application. This compound has the general formula:

$$R\!-\!\overset{O}{\overset{\|}{C}}\!-\!O\!-\!\overset{X}{\overset{|}{C}H}\!-\!CH_2\!-\!(O\overset{Y}{\overset{|}{C}H}\!-\!CH_2)_{\overline{m}}\!-\!SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Another surfactant that may be used is the salts of C8–C24 carboxylic acid (soap). Preferably, for reducing the soap irritation to skin, the concentration of C8–C24 carboxylate fatty acid soap is at or less than 10% of total bar composition. More preferably, concentration of the soap is at or below 4% of total bar composition. Most preferably, said carboxylic acid soap is excluded from the bar composition of the subject invention.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2\!-\!\overset{(R^3)_x}{\overset{|}{Y^{(+)}}}\!-\!CH_2\!-\!R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1 -carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1\!-\!\!\left[\!\!\begin{array}{c}O\\\|\\C\end{array}\!\!\right]\!\!-\!\!NH(CH_2)_{\overline{n}}\!\!\left.\!\!\right]_m\!\!-\!\!\underset{\underset{R^3}{|}}{\overset{\overset{R^2}{|}}{N^+}}\!\!-\!\!X\!\!-\!\!Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

$$R^1\!\!-\!\!\underset{\underset{R^3}{|}}{\overset{\overset{R^2}{|}}{N^+}}\!\!-\!\!CH_2CO_2^-$$

and amido betaines of formula:

$$R^1\!-\!CONH(CH_2)_{\overline{m}}\!\!-\!\!\underset{\underset{R^3}{|}}{\overset{\overset{R^2}{|}}{N^+}}\!\!-\!\!CH_2CO_2^-$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula $$R^1\!\!-\!\!\underset{\underset{R^3}{|}}{\overset{\overset{R^2}{|}}{N^+}}\!\!-\!\!(CH_2)_3SO_3^-$$

or $$R^1\!-\!CONH\,(CH_2)_{\overline{m}}\!\!-\!\!\underset{\underset{R^3}{|}}{\overset{\overset{R^2}{|}}{N^+}}\!\!-\!\!(CH_2)_3SO_3^-$$

where m is 2 or 3, or variants of these in which $-(CH_2)_3 SO^-_3$ is replaced by $$-CH_2\overset{\overset{OH}{|}}{C}HCH_2\,SO_3^-$$

In these formulae $R^1$, $R^2$ and $R^3$ are as discussed previously.

A further possibility is that the amphoteric detergent is a sulphobetaine of formula $$R^1\!\!-\!\!\underset{\underset{R^3}{|}}{\overset{\overset{R^2}{|}}{N^+}}\!\!-\!\!(CH_2)_3SO_3^-$$

or $$R^1\!-\!CONH(CH_2)_m\!\!-\!\!\underset{\underset{R^3}{|}}{\overset{\overset{R^2}{|}}{N^+}}\!\!-\!\!(CH_2)_3SO_3^-$$

where m is 2 or 3, or variants of these in which $-(CH_2)_3 SO_3^-$ is replaced by $$-CH_2\overset{\overset{OH}{|}}{C}HCH_2SO_3^-$$

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 0.1% to 15%, more preferably 0.1 to 10% by wt. of the composition.

In addition to one or more anionic and amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

(b) Emollient Oils and Humectants

The personal washing bar also contains 5% to 40%, preferably 10% to 25% total bar composition a liquid hydrophobic emollient oil, a liquid hydrophilic humectant or mixtures thereof.

Said liquid hydrophobic emollient oil has a solubility of less than 10%, preferably less than 5%, and most preferably less than 1% in water at 25° C.

Said liquid emollient oil has a melting temperature of less than 25° C. and has a viscosity less than $10^5$ centipoise, preferably less than 50,000 centipoise, most preferably less than 10,000 centipoise at 25° C. The defined melting temperature and viscosity range of said oil is a criticality since keeping the oil in a free flow liquid state is important for satisfactory bar mixing as well as for pouring into the bar mold when preferred cast melt process is applied. For example, above the viscosity range, oil becomes very thick, and this prevents the efficiently mixing of the bar ingredients at molten state (e.g., 85–125° C.), reduces the pourability of the melt, and causes bar in homogeneity and processing difficulties.

The emollient oil is selected from the group consisting of hydrocarbon oils, silicones, liquid diglycerides, liquid triglycerides, liquid di- and tri-glyceride derivatives, liquid hydrocarbon esters, silicones, sterols, lanolins and sunscreen oils.

Examples of hydrocarbon oils are mineral oil, petrolatum, C8–C24 straight or branched chain alkyl or alkenyl compounds.

Examples of liquid di- and tri-glycerides and their derivatives are sorbitol, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, milk glycerides and mixtures thereof.

Examples of silicone oil include dimethicone copolyol, and dimethylpolysiloxane.

Examples of hydrocarbon esters include isopropyl myristate and isocetyl palmitate.

Examples of the sunscreen oils include butyl methoxydibenzoylmethane (tradename: Parsol 1789), octyl methoxy cinnamate (tradename: Parsol MCX), benzophenone quat, niacinamide, padimate 0, P-proline.

It is more preferred that the emollient oil is selected from liquid di- and tri-glycerides and their derivatives.

The liquid hydrophilic humectant, when used, has a solubility of greater than or equal to 50% wt. in water at 25° C.

Said liquid humectant has a melting temperature at less than 25° C. and has a viscosity at less than 5000 centipoise, preferably less than 1000 centipoise.

The liquid humectant is selected from polyols consisting of glycerol, glycerin, propylene glycol, liquid polyalkylene glycols such as polypropylene glycols, polyethylene glycols with molecular weight less than 1000 (such that they are in liquid state at 25° C.), ethyl hexanediol, and hexylene glycols.

(c) Solid Amphiphilic Polyol Esters

The bar of the subjective invention also comprises 15% to 70%, preferably 20% to 50%, total composition of a solid amphiphilic polyol ester.

Said amphiphilic polyol ester is specified by its hydrophilic lipophilic balance (HLB) value that is defined by Becher and Schick and by Marszall in Chapter 8 and Chapter 9 of Nonionic Surfactants—Phase Chemistry, Surfactant Sci. Series, Vol. 23, P439–549, which is hereby incorporated by reference into the subject application as reference. Said solid, amphiphilic polyol ester has a hydrophilic-lipophilic balance (HLB) value between 2 and 1 5, preferably between 2.5 and 10, and most preferably between 3 and 8. The HLB range of the polyol ester is a criticality because below the range, the polyol ester can bind too tightly with the oil (b) and not allow the oil to be released to the aqueous solution, which prevents the oil to be delivered to the skin; and above the HLB range, the polyol ester does not have the capability to structure the emollient oil and the humectant described in (b) in the solid bar matrix and causes oil leakage and separation from the bulk.

Said polyol ester has a melting temperature between 40° C. and 90° C., preferably at between 45° C. and 70° C.; such that the matrix formed by the polyol ester to trap the oil is in the solid form in the bar under in-use condition.

The weight ratio of the said polyol ester to the sum of the emollient oil and the humectants, both described in (b), is greater than or equal to 1: 1, preferably greater than or equal to 1.5:1; this weight ratio is a criticality because below this ratio, the oil and the humectant can not be satisfactorily contained in the solid matrix of the bar, which leads to oil leakage and separation from the bulk.

The said solid, amphiphilic polyol ester is defined as a polyol esterified or partially esterified by an organic acid that can be represented by $$POL-O-\overset{O}{\underset{\parallel}{C}}-R$$

in which POL is a polyol moiety, R is a hydrophobic moiety, and one or more {—O—(C=O)—R} functional groups are chemically attached to one or more hydroxy groups of the polyol moiety.

For example, the polyol moiety (POL) may be derived from glycerol, glycerin, propylene glycol, polypropylene glycols, ethylene glycol, polyethylene glycols, ethyl hexanediol, hexylene glycols and pentaeryrthritylor mixtures thereof.

The hydrophobic group R is selected from the derivatives of alkyl, aryl, alkylaryl, alkylene, acyl, and fat and oil derivatives or mixtures thereof. Preferably R is the derivative of a C8–C22 straight or branched chain alkyl functioning group, most preferably a C12–C22 alkyl functioning group.

Examples of said solid, amphiphilic polyol ester include glycerin fatty esters and glycerol esters, such as glyceryl monolaurate (from Henkel under the tradename of Monomuls 90L-12) and glyceryl monostearate (from Stepan under the tradename of GMS Pure); alkylene glycol fatty esters, such as ethylene glycol monostearate and ethylene glycol monolaurate (from RP under the tradename of Alkamuls); pentaeryrthritylfatty esters such as pentaeryrthritylstearate; polyglycerin fatty esters such as hexaglyceryl tristearate. The physical properties of a few suitable polyol esters were listed in Table 1.

TABLE 1

Examples and properties of the suitable polyol esters for the subject invention

| Polyol Ester | Melting temperature (° C.) | HLB Value | Tradename/supplier |
|---|---|---|---|
| Glyceryl monolaurate | 56–65 | 4.9 | Monomuls 90L-12/ Henkel Corp. |
| Glyceryl monostearate | 56–65 | 3.8 | Kessco GMS Pure/ Stepan |
| Ethylene glycol stearate | 52–56 | 2.9 | Kessco EGMS 70/ Stepan |

(d) Optional Structurants

The compositions may also contain 0 to 30% by wt., preferably 5 to 20% by wt. of an optional structurant and/or filler. Such structurants can be used to enhance the bar integrity, improve the processing properties, and enhance desired user sensory profiles.

The total weight percentage of said optional structurants and/or filler has to be less than the weight percentage of the said polyol ester defined in (c). This specification on the upper limit of the optional structurants is a criticality because above this range, the bar has its oil structuring capability reduced, which causes oil leakage and/or oil phase separation from the bulk; or the bar has its oil releasing capability reduced, which prevents the oil release into the aqueous washing liquor and deliver to the skin via the personal washing route.

Said optional structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

The optional structurant can also be polyalkylene glycol with molecular weight between 2000 and 20,000, preferably between 3000 and 10,000. Those PEGs are commercially available, such as those marketed under the tradename of CARBOWAX SENTRY PEG 8000 or PEG 4000 by Union Carbide.

The optional structurants that can be used include starches, preferably water soluble starches such as maltodextrin and polyethylene wax or paraffin wax.

The optional structurant can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm$^{(R)}$ (PEG modified glyceryl cocoate, palmate or tallowate) from Rewo Chemicals.

The optional structurants also include Amerchol Polymer HM 1500 (Nonoxynyl Hydroethyl Cellulose).

Other Optional ingredients

In addition, the bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL 1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330- Polyquaternium 39; and Jaguar$^{(R)}$ type conditioners.

Polyethylene glycols as conditioners which may be used include:

Polyox WSR-205 PEG 14 M,

Polyox WSR-N-60 K PEG 45 M, or

Polyox WSR-N-750 PEG 7 M.

Another ingredient which may be included are exfoliants such as polyoxyethylene beads, walnut shells and apricot seeds.

Another ingredient which may be included are 0–20% zinc oxides and titanium oxide for the purpose of protecting the skin from sun damage.

The present invention is set forth in greater detail in the examples which follow. The examples are for illustration purposes only and are not intended to limit the scope of the claims in any way.

All percentages in the examples and specification, unless indicated otherwise, are intended to be percentages by weight.

EXAMPLES

Protocol

Mildness Assessments

Zein dissolution test was used to preliminary screen the irritation potential of the formulations studied. In an 8 oz. jar, 30 mLs of an aqueous dispersion of a formulation were prepared. The dispersions sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

The 3–4 Day Patch Test was used to evaluate skin mildness of aqueous dispersions containing 1% DEFI active (sodium cocoyl isethionate) and different levels of the structurant/coactives. Patches (Hilltop(R) Chambers, 25 mm in size) were applied to the outer upper arms of the panelists under bandage type dressings (Scanpor(R) tape). After each designated contact periods (24 hrs. for the first patch application, 18 hrs. for the second, third or fourth applications), the patches were removed and the sites were visually ranked in order of severity (erythema and dryness) by trained examiners under consistent lighting.

Formulation Processing

Bar solids were prepared by a cast melt process. First, the components were mixed together at 80–120° C. in 100 g to 2000 g scale in a liquid mixer for 30–60 minutes using an overhead stir. Then rest of the components were added, and the water level was adjusted to approximately 8–15 wt %. The batch was covered to prevent moisture loss and was mixed for about 15–45 minutes. Then the cover was removed, and the mixture was allowed to dry. The moisture content of the samples was taken at different times during the drying stage and was determined by Karl Fisher titration with a turbo titrator. At the final moisture level (0–3%), the mixture in the form of free-flow liquid was dropped to bar molds and was allowed to be cooled at room temperature for 4 hours. Upon solidification, the molten mixture in the mold was casted into bar solids.

Example 1
Advantages of Using Polyol Ester as Oil Structurant in Comparison with PEG 8000 and Palmitic/stearic Acid Carrying 20% sunflower seed oil, a bar structuring system comprised of Polyol ester (glyceryl monolaurate), PEG 8000 and fatty acid was selected to test the formulation space for satisfactory oil structuring and releasing capabilities.

Comparative 1

Shown in the ternary phase diagram (FIG. 1), samples containing high levels of PEG 8000 (i.e., concentration of PEG 8000 is above 50% total structuring system) separated into an oily top layer and a bottom layer comprised of the rest. Cooling the PEG-rich samples to room temperature resulted in tacky solids with oil leaking out. This implies that PEG 8000 is not suitable as the major structurant for a high oil bar, which is consistent with the findings discussed in Example 2.

Comparative 2

Figure 1:
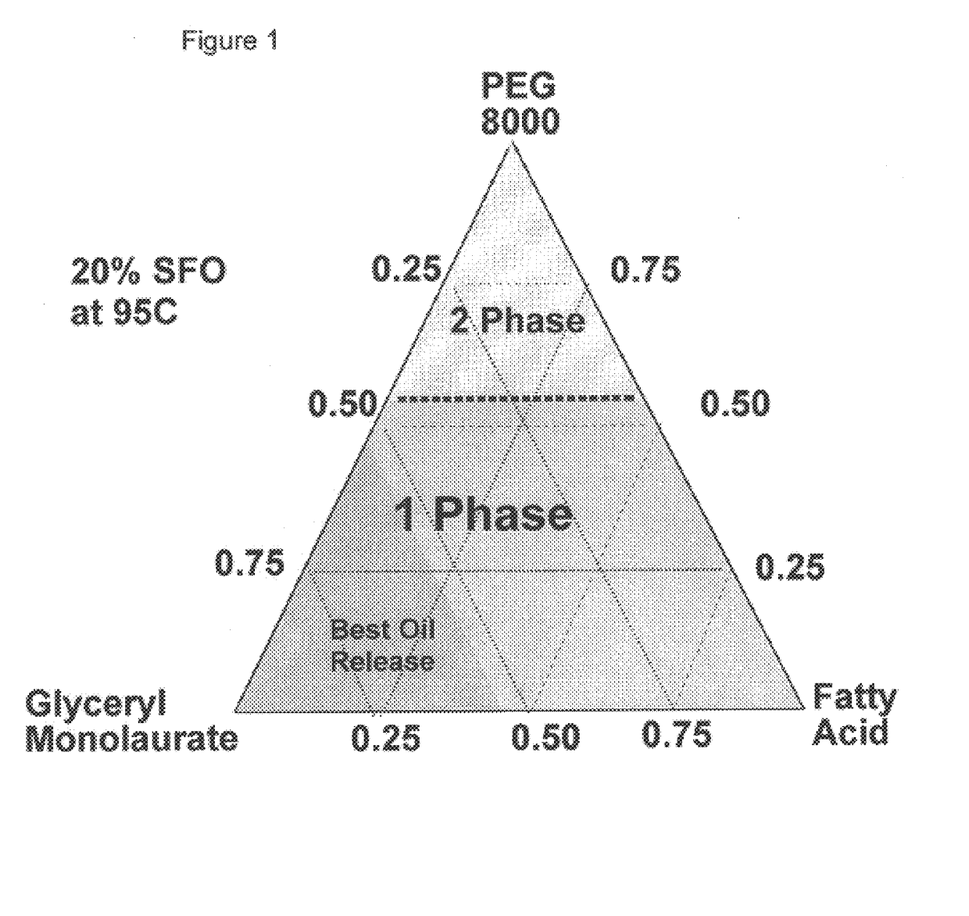
FIG. 1 presents the phase diagram of PEG 8000, fatty (stearic/palmitic) acid and polyol ester (glyceryl monolaurate) at 95° C. The ternary system contains sunflower seed oil at fixed level of 20% wt (i.e., the total concentration of PEG 8000, fatty acid and the glyceryl monolaurate equals to 80% total composition).

In the fatty acid rich region of the FIG. 1 (i.e., concentration of FA is above 60% total structuring system), samples formed single isotropic liquids at 95° C. Cooling those samples to 25° C. resulted in firm, crisp solids. However, there was no oil released from the solids into water, as observed under optical microscopy, and this was not desired for benefit delivery. Thus the traditional hydrophobic binders, such as stearic/palmitic acid or wax are not ideal as the major structurants for the high oil bars.

Invention

In the polyol ester rich region (i.e., glyceryl monolaurate concentration is above 50%), samples formed single-phase isotropic liquids at 95° C. Cooling the molten mixtures to 25° C. resulted in firm, crisp solids, which permitted oil release into aqueous phase. Thus monoglyceride should be used as the major structurant (i.e., 50% and above of the total bar structuring system) for the optimum oil-carrying and releasing.

Example 2
Formulations of Invention and Comparative Bars

Formulation F-1, F-2 and F-3 contains 20% sunflower seed oil and primarily structured by polyol esters such as glyceryl monolaurate and glyceryl monostearate (both are polyol esters). The major lathering ingredients in those formulations are SLES and CAP betaine. As a result, F-1 provides lotion like, oily lather, as well as strong after-wash moisturizing skin feel. F-2 provides the lather and skin feel similar to F-1, but the bar is significantly harder than F-1. F-3 provides the lather and skin feel similar to F-1 and F-2 but with significantly less mush. F-4 uses ethylene glycol monostearate (a polyol ester) to structure the bar to achieve a unique oily after-wash skin feel. F-5 contains sodium cocoyl isethionate as the major lathering surfactant. In combination with the sunflower seed oil and the monoglycerides, the bar F-5 provides more creamy, rich lather and retains the oily skin feel. Bar F-6 of the invention incorporated 20% glycerin instead of the sunflower seed oil. The polyol ester (glyceryl monostearate) structured the 20% glycerin liquid in the bar without leaking or phase separation, and the bar provides a unique moisturizing skin feel and is ultra-mild to the skin.

C-1 is a comparative bar containing no oil and no polyol ester, thus it lacks the oily feel provided by the bars of the subject invention (i.e., F1 through F-6). The bar is more irritative to skin when compared with the invention bars (see Example 3 and Example 4).

In contrast to the invention bars that are structured primarily by the polyol esters, C-2 is structured by PEG 8000 and stearic/palmitic (fatty) acid, and the weight ratio of glyceryl monolaurate to the sum of PEG 8000 and fatty acid is slightly less than 1 (i.e., 26.841 (25+3.67)=0.94). As a result, a portion of the sunflower seed oil separated from the bulk during mixing, and oil pooling was found in the finished bar. Therefore, it is a criticality of the subject invention that the polyol ester has to be used as the primary structurant to trap the oil in the solid matrix of the bar.

TABLE 2

Formulations of the invention and comparative bars

| Ingredients | F-1 wt % | F-2 wt % | F-3 wt % | F-4 wt % | F-5 wt % | F-6 wt % | C-1 wt % | C-2 wt % |
|---|---|---|---|---|---|---|---|---|
| Sodium Cocoyl isethionate | 5.0 | 8.0 | 8.0 | 8.0 | 27.0 | 0 | 27.0 | 12.5 |
| Sodium lauryl sulfate | 10.0 | 6.0 | 6.0 | 6.0 | 0 | 10.0 | 0 | 5.0 |
| Cocoamidopropyl betaine | 10.0 | 6.0 | 6.0 | 6.0 | 5.0 | 10.0 | 5.0 | 5.0 |
| Glyceryl monolaurate | 19.0 | 40.65 | 0 | 0 | 27.6 | 0 | 0 | 26.84 |
| Glyceryl monostearate | 19.0 | 0 | 40.65 | 0 | 0 | 41.0 | 0 | 0 |
| Stearic/ palmitic acid | 5.0 | 2.35 | 2.35 | 0 | 8.4 | 5.0 | 17.0 | 3.67 |
| Ethylene glycol monostearate | 0 | 0 | 0 | 40.65 | 0 | 0 | 0 | 0 |
| PEG 8000 | 8.0 | 15.0 | 15.0 | 15.0 | 10.0 | 10.0 | 22.0 | 25.0 |
| Maltodextrin | 0 | 0 | 0 | 0 | 0 | 0 | 10.0 | 0 |
| PEG 300 | 0 | 0 | 0 | 0 | 0 | 0 | 2.0 | 0 |

TABLE 2-continued

Formulations of the invention and comparative bars

| Ingredients | F-1 wt % | F-2 wt % | F-3 wt % | F-4 wt % | F-5 wt % | F-6 wt % | C-1 wt % | C-2 wt % |
|---|---|---|---|---|---|---|---|---|
| PEG 1450 | 0 | 0 | 0 | 0 | 0 | 0 | 3.0 | 0 |
| Sodium stearate | 4.0 | 0 | 0 | 0 | 0 | 0 | 6.0 | 0 |
| Sodium isethionate | 0.2 | 0.4 | 0.4 | 0.4 | 1.2 | 0 | 2.2 | 0.5 |
| Glycerin | 0 | 0 | 0 | 0 | 0 | 20.0 | 0 | 0 |
| Sunflower seed oil | 20.0 | 20.0 | 20.0 | 20.0 | 20.0 | 0 | 0 | 20.0 |
| Water | | 1.6 | 1.6 | 1.6 | 0.8 | 4.0 | 5.8 | 1.5 |

Example 3
Ultra Skin Mildness of the Bar Containing High Level of Oil and the Polyol Esters Table 3 shows the weight percent of the Zein protein dissolved by cleansing bar formulations shown in Table 2, Example 2. Formulation F-1 and F-5 (invention) were found to dissolve no detectable amount of zein (<<10%); in contrast, Formulation C-1 (comparative) dissolved about 16% Zein protein. The results show that the bars of the invention (F-1 & F-5) containing a high level of sun flower seed oil (i.e. 20%) and monoglycerides (a polyol ester) have ultra low irritation potential to skin. The comparative bar C-1 w/o the oil and the polyol ester may have a significantly higher skin irritation potential when compared with the F-1 and F-5 bars of the invention.

TABLE 3

The Results of the Zein Testing

| Bar Formulation | Zein Protein % Dissolved |
|---|---|
| F-1 (Invention) | <<10 |
| F-5 (Invention) | <<10 |
| C-1 (Comparative) | 16.0 |

Example 4

As shown in Table 4, In-vivo Human Skin Patch Testing indicates that the bar of invention (i.e., F-1 and F-6 of Example 2) is significantly milder than the comparative bar (i.e., C-1 of Example 2). Not to be bound by the theory, the invention bar F-1 and F-6 contains high level of emollient oil or humectant and the monoglyceride (also an emollient), which in combination contribute to the skin mildness. Also the monoglyceride (a polyol ester) also structured liquid ultra mild surfactants such as SLES and CAP betaine in the bar, which reduced the skin irritation.

TABLE 4

In-vivo Human Skin Patch Test Results

| Bar Formulation | Patch Test Score; Sum of Ranks at Day-4 (lower sum --> more irritative, a difference of approximately 18 in the sum of ranks is necessary for a test material to be significantly different from the control material (i.e., 90% confidence level)). |
|---|---|
| F-1 (Invention) | 52.0 |
| F-6 (Invention) | 81.0 |
| C-1 (comparative control) | 28.0 |

Example 5

The high oil bars developed in the subject invention can be used to carry sun-protecting oils, and the sun-protecting oils can be delivered from the bars to skin via skin cleansing. In formulation F-7 and F-8, Parsol MCX (a UV absorbing oil, sun protecting agent) is incorporated. Both bars provide oily skin feel. F-7 provides a lotion like lather, and F-8 provides creamy and rich lather.

| FULL CHEMICAL NAME OR CTFA NAME | F-7 % wt. | F-8 % wt. |
|---|---|---|
| Sodium cocoyl isethionate | 7.93 | 27.0 |
| Palmitic/Stearic acid | 2.44 | 8.68 |
| Cocamidopropyl Betaine | 5.95 | 5.00 |
| Ethylhexyl p-methoxycinnamate or (Parsol MCX) | 19.83 | 20.0 |
| PEG 8000 | 14.87 | 10.0 |
| Glycerol monostearate | 40.3 | 26.6 |
| sodium lauryl ether sulfate-3eo | 5.95 | — |
| target Water | 1.0 | 0.57 |
| Fragrance(Dove Shower Gel) | 0.5 | 0.29 |
| Sodium isethionate | 0.49 | 1.15 |
| Sodium chloride | 0.4 | 0.37 |
| Titanium dioxide | 0.3 | 0.30 |
| EDTA | 0.02 | 0.02 |
| EHDP | 0.02 | 0.02 |
| Total | 100 | 100 |

We claim:

1. A solid skin cleansing bar comprising:
   (a) about 15% to 70% total bar composition surfactant or mixtures of surfactants wherein at least one surfactant is an anionic surfactant; and
   (b) 5% to 40% total bar composition of a liquid hydrophobic emollient oil or a liquid hydrophilic humectant or mixtures thereof;
      said liquid hydrophobic emollient oil having a water solubility less than 10% in water at 25° C.; said liquid emollient oil having a melting temperature of less than 25° C.; said oil having a viscosity less than $10^5$ centipoise at 25° C.;
      and wherein said emollient oil is selected from the group consisting of C8–C24 hydrocarbon oils; silicones; liquid diglycerides, liquid triglycerides and liquid di- and tri-glyceride derivatives; vegetable oils and vegetable oil derivatives to the extent not covered by other recited categories; sterols; lanolins; and mixtures thereof;
      said liquid hydrophilic humectant having a solubility of greater than or equal to 50% wt. in water at 25° C.; said liquid humectant having a melting temperature of less than 25° C. and having a viscosity of less than 5000 centipoise at 25° C.;
      and wherein said humectant is selected from the group consisting of glycerol, glycerin, C1–C10 alkylene glycols, polyalkylene glycols, ethyl hexanediol, and hexylene glycols;
   (c) 15% to 70% total composition of a solid, amphiphilic polyol ester having the following structure described as POL represents polyol moiety, R represents an organic hydrophobic group, and one or more —O—(C=O)—R functional groups are chemically attached to one or more hydroxy groups in the polyol moiety to achieve partial or total esterification;

said solid, amphiphilic polyol ester having the hydrophilic-lipophilic balance (HLB) number at between 2 and 15, said polyol ester having melting temperature at between 40° C. and 90° C.;

and wherein the weight ratio of the said polyol ester (c) to the sum of the said emollient oil and/or humectant (1(b)) is greater than or equal to 1:1.

2. A composition according to claim 1 (a), wherein the surfactant or mixture of the said surfactants comprise of 10% to 60% total composition.

3. A composition according to claim 1(a), wherein the surfactant or mixture of the said surfactants comprise of 15% to 40% total composition.

4. A composition according to claim 1(b), wherein the hydrophobic emollient oil and/or the liquid humectant or the mixtures thereof comprise of 10% to 25% total composition.

5. A composition according to claim 1(c), wherein the polyol ester or mixture of the said polyol esters comprise 20% to 50% total composition.

6. A composition according to claim 1(c), wherein the polyol ester has a melting temperature of between 45° C. and 70° C.

7. A composition according to claim 1(c), wherein the polyol ester has a HLB value between 2.5 and 10.

8. A composition according to claim 1 (c), wherein the polyol ester has a HLB value between 3 and 8.

9. A composition according to claim 1 (c), wherein the weight ratio of the polyol ester to the sum of the emollient oil and humectant (claim 1 (b)) is greater or equal to 1.5:1.

10. A composition according to claim 1(c), wherein the weight ratio of the polyol ester to the sum of the emollient oil and humectant (claim 1 (b)) is greater or equal to 2:1.

11. A composition according to claim 1, wherein the glycerin fatty ester is glyceryl monostearate or glyceryl monolaurate.

12. A composition according to claim 1, wherein the alkylene glycol fatty ester is ethylene glycol monostearate or ethylene glycol monolaurate.

13. A composition according to claim 1, wherein the pentaeryrthritylfatty ester is selected from pentaerythrityl monostearate and pentaerythrityl monolaurate.

14. A composition according to claim 1(b), wherein the humectant has a viscosity less than 5000 centipoise at 25° C.

15. A composition according to claim 1(b), wherein the hydrophobic emollient oil has a viscosity less than 1000 centipoise at 25° C.

16. A composition according to claim 1(b), wherein the hydrophobic emollient oil has a viscosity less than 500 centipoise at 25° C.

17. A composition according to claim 1(b), wherein the hydrophobic emollient oil has a solubility less than 5% wt. in water at 25° C.

18. A composition according to claim 1(b), wherein the hydrophobic emollient oil has a solubility less than 1% wt. in water at 25° C.

19. A composition according to claim 1, further comprising 0 to 30% total bar composition of an optional structurant, and the total weight percentage of said optional structurant is less than the total weight percentage of said polyol ester described in (1(c)); and said optional structurant is a solid selected from $C_8$–$C_{24}$ straight and saturated fatty acid or ester derivative thereof; and/or $C_8$–$C_{24}$ straight and saturated, alcohol or ether derivatives thereof; polyalkylene glycol with molecular weight between 2000 and 20,000; starches; water soluble polymers chemically modified with hydrophobic moiety or moieties, and mixtures thereof.

20. A composition according to claim 19, wherein the optional structurant comprises 5% to 20% total bar composition.

21. A composition according to claim 1(b), wherein the hydrophobic emollient oil is a UV absorbing sunscreening (sun protecting) oil.

* * * * *